(12) United States Patent
Yokozaki et al.

(10) Patent No.: US 9,372,155 B2
(45) Date of Patent: Jun. 21, 2016

(54) ROE MATURITY DETERMINATION DEVICE

(75) Inventors: Yasuhiro Yokozaki, Ehime (JP);
Masami Okayama, Ehime (JP);
Gentaro Kakemizu, Ehime (JP);
Masanori Tsuruta, Tokyo (JP); Takeshi Suzuki, Tokyo (JP); Hiroyoshi Koizumi, Tokyo (JP)

(73) Assignee: MARUHA NICHIRO CORPORATION, Tokyo (JP)

( * ) Notice: Subject to any disclaimer, the term of this patent is extended or adjusted under 35 U.S.C. 154(b) by 999 days.

(21) Appl. No.: 13/508,227

(22) PCT Filed: Nov. 1, 2010

(86) PCT No.: PCT/JP2010/069411
§ 371 (c)(1),
(2), (4) Date: May 4, 2012

(87) PCT Pub. No.: WO2011/055698
PCT Pub. Date: May 12, 2011

(65) Prior Publication Data
US 2012/0224055 A1 Sep. 6, 2012

(30) Foreign Application Priority Data

Nov. 9, 2009 (JP) .................................. 2009-256067
Nov. 24, 2009 (JP) .................................. 2009-266184

(51) Int. Cl.
*H04N 7/18* (2006.01)
*G01N 21/59* (2006.01)
(Continued)

(52) U.S. Cl.
CPC ............. *G01N 21/59* (2013.01); *A22C 17/0073* (2013.01); *A22C 25/04* (2013.01); *G01N 21/84* (2013.01); *G01N 33/12* (2013.01); *G01N 2021/845* (2013.01)

(58) Field of Classification Search
CPC ...... G01B 11/022; G01B 11/024; H04N 7/18; H04N 7/181; G01C 15/00; C08K 5/1575; C08K 2201/014; C08L 23/02; G01J 3/02; G01J 3/0264; G01J 3/0272; G01J 3/0291; G01J 3/2803; G01J 3/0259; G01J 3/0267; G01J 3/26; G01J 3/51; G01J 3/513; G01J 2003/1213
See application file for complete search history.

(56) References Cited

U.S. PATENT DOCUMENTS 4,586,613 A * 5/1986 Horii .............................. 209/556
4,976,356 A * 12/1990 Mizuno et al. ................ 209/539
(Continued)

FOREIGN PATENT DOCUMENTS

JP      04-140647 A      5/1992
JP      09-264851 A     10/1997
(Continued)

OTHER PUBLICATIONS

Abdullah et al. "Stepwise discriminant analysis for colour grading of oil palm using machine vision system," Institution of Chemical Engineers Trans ICemE, vol. 79, Part C, Dec. 2001, pp. 223-231 (hereinafter NPL2).*

(Continued)

*Primary Examiner* — Sath V Perungavoor
*Assistant Examiner* — Howard D Brown, Jr.
(74) *Attorney, Agent, or Firm* — Brinks Gilson & Lione (57) ABSTRACT

Roe W is loaded on a loading tray 6, the roe W is irradiated with light from light irradiation means 11, and an image of at least a part of the roe W irradiated with light from the light irradiation means 11 is taken by image pickup means 12. Image processing of the image Pa taken by the image pickup means 12 is performed to measure a light transmissive value of the light passing through the roe W; and maturity of the roe W is determined based on the measured light transmissive value. This enables a roe maturity determination device and a roe maturity determination method capable of determining precisely roe maturity.

16 Claims, 8 Drawing Sheets

(51) Int. Cl.
*A22C 17/00* (2006.01)
*A22C 25/04* (2006.01)
*G01N 33/12* (2006.01)
*G01N 21/84* (2006.01)
*G01N 21/00* (2006.01)
*A01K 43/00* (2006.01)

(56) References Cited

U.S. PATENT DOCUMENTS

| | | | | |
|---|---|---|---|---|
| 5,013,906 | A | * | 5/1991 | Miyakawa et al. ........ 250/223 R |
| 5,173,737 | A | * | 12/1992 | Mitchell .............. G01N 33/085 356/53 |
| 5,335,791 | A | * | 8/1994 | Eason ........................... 209/588 |
| 5,845,002 | A | * | 12/1998 | Heck et al. .................... 382/110 |
| 6,610,953 | B1 | * | 8/2003 | Tao et al. ....................... 209/577 |
| 2003/0035108 | A1 | * | 2/2003 | Taniguchi ............ G01N 21/359 356/432 |
| 2007/0024843 | A1 | | 2/2007 | Hebrank et al. |
| 2008/0169225 | A1 | * | 7/2008 | De Greef ....................... 209/576 |

FOREIGN PATENT DOCUMENTS

| | | |
|---|---|---|
| JP | 2004-101204 A | 4/2004 |
| JP | 2004-177309 A | 6/2004 |
| JP | 2006-197893 A | 8/2006 |
| JP | 2007-303939 A | 11/2007 |
| JP | 2009-503509 A | 1/2009 |

OTHER PUBLICATIONS

Croft et al. "Sensor Technology Integration in an Intelligent Machine for Herring Roe Grading," IEEE/ASME Transactions on Mechatronics, vol. 1, No. 3, Sep. 1996, pp. 204-215.*
Abdullah et al. "Stepwise discriminant analysis for colour grading of oil palm using machine vision system," Institution of Chemical Engineers Trans ICemE, vol. 79, Part C, Dec. 2001, pp. 223-231.*
Croft et al. "Sensor Technology Integration in an Intelligent Machine for Herring Roe Grading," IEEE/ASME Transactions on Mechatronics, vol. 1, No. 3, Sep. 1996, pp. 204-215 (hereinafter NPL1).*
International Search Report for International Application No. PCT/JP2010/069411, dated Feb. 15, 2011, 2 pages.

* cited by examiner

(Light source: Halogen lamp)

| Mature roe △ | 58 | 53 | 85 | 73 | 58 | 79 | 81 | 73 | 84 | 53 |
|---|---|---|---|---|---|---|---|---|---|---|
| Post-mature roe ○ | 129 | 132 | 131 | 143 | 124 | 130 | 112 | 101 | 105 | 130 |

ROE MATURITY DETERMINATION DEVICE

This application is a 371 application of PCT/JP2010/069411 having an international filing date of Nov. 1, 2010, which claims priority to JP2009-256067 filed Nov. 9, 2009 and JP2009-266184 filed Nov. 24, 2009, the entire contents of which are incorporated herein by reference.

TECHNICAL FIELD

The present invention relates to a roe maturity determination device and a roe maturity determination method to determine maturity of roe taken out from a fish body.

BACKGROUND ART

Frozen pollack roe, which is an ingredient of salted cod roe and seasoned cod roe, is an ovary of pollack roe. Pollack is mainly caught at Northern fishing grounds around Alaska, U.S. and the Kamchatka, Russia, and in any case they are freezing-processed at onshore factories in isolated islands or on board. Conventionally frozen pollack roe is manufactured as in the following (1) to (4), for example:

(1) caught pollack is loaded one by one on a tray for automatic processor;

(2) the head of a pollack is cut by the automatic processor, and roe as well as offal are taken out with a roe scraping device:

(3) the roe scraped out with the offal is manually separated from the offal by an operator, for example;

(4) the roe separated from the offal is classified manually one by one in accordance with their shapes, colors, maturity and weight; and (5) the classified roe of specified weight is frozen and packed as a product.

In the above step (4), the classification is performed on the basis of the following selection criteria (a) to (d):

(a) shapes: integrity or cut;

(b) colors: light color, dark color, brownish burnt or a bile adhered state;

(c) maturity: premature, mature or post-mature; and (d) weight: after the selection based on (a) to (c), selected by weight.

In the determination of the above (c) for maturity, operators touch the roe with their hands to check the feel of the roe or visually determine the state of eggs of the pollack roe. Pollack roe is caught between January and April, and premature to mature pollack roe is caught in January and February, and mature to post-mature pollack roe is caught in March and April. Maturity of pollack roe varies with each fish, which is one of important elements for classification.

Patent Document 1 discloses a technique for a fish body treatment device to take roe or the like out from a fish body. Patent Document 1: JP Patent Application Publication No. 2006-197893 A

DISCLOSURE OF THE INVENTION

Problem to be Solved by the Invention

In the case of the aforementioned conventional determination on pollack roe maturity, however, the determination is based on sensory evaluation by a person such as the sense of touch or visually checking. Therefore, determination results often are different with each person, and so it is difficult to perform precise classification based on the maturity. Such a problem is not limited to pollack roe but is applied to roe generally.

In view of the above respects, it is an object of the invention to provide a roe maturity determination device and a roe maturity determination method capable of uniformly determining the maturity of roe.

Means for Solving the Problem

In order to solve the aforementioned problems, a roe maturity determination device of the present invention includes: a loading portion on which roe is loaded; light irradiation means that irradiates the roe loaded on the loading portion with light; image pickup means that takes an image of light irradiated from the light irradiation means and passing through the roe; and determination means that determines maturity of the roe on a basis of the image taken by the image pickup means.

According to the roe maturity determination device of the present invention, an image of light irradiated from the light irradiation means and passing through roe is taken, and on the basis of the taken image, maturity of the roe is determined. Therefore, a uniform determination result can be always obtained. Accordingly, the quality of roe can be made stable.

Preferably the roe maturity determination device according to the present invention further includes image processing means that performs image processing of the taken image to extract an image including at least a part of the roe from the taken image, thus creating a roe image, and measures, on a basis of the created roe image, a light transmissive value of light passing through the roe. The determination means may determine the maturity on a basis of the light transmissive value measured by the image processing means.

In the roe maturity determination device according to the present invention, the light transmissive value includes at least one of lightness, color saturation and hue. Preferably, the image processing means may calculate an average of light transmissive values of light passing through a predetermined area range of the roe on a basis of the roe image, and the determination means may determine the maturity of the roe on a basis of the average of light transmissive values calculated by the image processing means.

Preferably the determination means may compare the average with a predetermined threshold to determine, on a basis of a result of the comparison, whether the roe is mature or post-mature. Preferably when the average is lower than the threshold, the determination means may determine that the roe is mature, and when the average is the threshold or higher, the determination means may determine that the roe is post-mature.

Preferably the determination means may determine to which one of a plurality of predetermined maturity ranks the average corresponds, and decides, on a basis of a result of the determination, the maturity of the roe. Preferably the determination means may use three types of maturity ranks including a premature roe rank, a mature roe rank and a post-mature roe rank as the plurality of maturity ranks to determine the maturity of the roe. Preferably the determination means may determine to which one of light transmissive value regions, each corresponding to the premature roe rank, the mature roe rank or the post-mature roe rank, the average corresponds, and may determine, on a basis of a result of the determination, that the roe is any one of the premature roe, the mature roe and the post-mature roe.

Preferably in the roe maturity determination device according to the present invention, the loading portion may include a plate member made of a light transmissive material, the light irradiation means may irradiate the loading portion with light from any one side of above and below the loading portion, and the image pickup means may take the image from the other side of the loading portion. Further preferably the light irradiation means may be disposed below the loading portion so as to let light pass through the loading portion to irradiate the roe with the light, and the image pickup means may be disposed above the loading portion.

Preferably in the roe maturity determination device according to the present invention, the image pickup means may take a color image as the image.

In order to solve the aforementioned problems, a roe maturity determination method of the present invention includes the steps of: loading roe on a loading portion; irradiating the roe with light from light irradiation means; taking an image of the light irradiated from the light irradiation means and passing through the roe by image pickup means; performing image processing of the image taken by the image pickup means to measure a light transmissive value of the light passing through the roe; and determining maturity of the roe on a basis of the measured light transmissive value.

A roe maturity determination device of the present invention is configured to irradiate roe with light from below the roe, take an image of the irradiated light passing through the roe from above the roe and determine maturity of the roe on a basis of the taken image. The roe maturity determination device includes: a loading tray made of a light transmissive material, on which the roe is loaded; conveyance means that moves horizontally below the loading tray to convey the loading tray; supporting means provided between the conveyance means and the loading tray to support the loading tray above the conveyance means, the supporting means defining a space between the conveyance means and the loading tray, the space extending over a conveyance direction of the loading tray and having one opening side in a lateral direction with reference to the conveyance direction; and light irradiation means disposed at a height between the conveyance means and the loading tray, the light irradiation means protruding from one side of a lateral direction of the loading tray to the other side of the lateral direction so that the light irradiation means can pass through the space and emit light upwardly.

According to the roe maturity determination device of the present invention, the supporting means defines a space between the conveyance means and the loading tray, the space extending over a conveyance direction of the loading tray and having one opening side in a lateral direction with reference to the conveyance direction; and the light irradiation means is disposed at a height between the conveyance means and the loading tray, the light irradiation means protruding from one side of a lateral direction of the loading tray to the other side of the lateral direction so that the light irradiation means can pass through the space and emit light upwardly. With this configuration, as the loading tray is conveyed by the conveyance means, the light irradiation means can be passed through the space. At this time, light can be applied directly to the loading tray from below the loading tray.

Accordingly, the distance between the light irradiation means and the roe on the loading tray can be shortened, and the roe on the loading tray can be irradiated with sufficient amount of light so that the light passes through the roe. Therefore, an image of the light irradiated from the light irradiation means and passing through the roe can be taken easily, and maturity of the roe can be determined on the basis of the taken image.

In the roe maturity determination device according to the present invention, preferably the supporting means includes slanting means to slant the loading tray in the lateral direction, the slanting means being capable of changing a position of the loading tray from a loading position state to load the roe thereon to an output position state to let the roe out to a side of the conveyance means.

According to the roe maturity determination device of the present invention, even when slanting means is provided between the conveyance means and the loading tray, the light irradiation means can be disposed below the loading tray and light can be applied directly to the loading tray from below the loading tray. Accordingly, the distance between the light irradiation means and the roe on the loading tray can be shortened, and the roe on the loading tray can be irradiated with sufficient amount of light so that the light passes through the roe. Therefore, an image of the light irradiated from the light irradiation means and passing through the roe can be taken easily, and maturity of the roe can be determined on the basis of the taken image.

Preferably in the roe maturity determination device according to the present invention, the light irradiation means may include: a light source; a light emission portion that receives light from the light source and emits light; and an optical fiber cable to transmit light from the light source to the light emission portion.

According to the roe maturity determination device of the present invention, light can be transmitted from the light source to the light emission portion via the optical fiber cable, and therefore the light source can be provided at a position away from the light emission portion. As a result, transmission of heat of the light source to the loading tray or the roe on the loading tray can be prevented.

Preferably in the roe maturity determination device according to the present invention, the light source of the light irradiation means may be disposed at a position higher than the loading tray. According to the roe maturity determination device of the present invention, since the light source is provided at a position higher than the loading tray, adhesion of water from the roe to the light source can be prevented, and so a short of a power supply for the light source can be prevented.

This application claims the benefit of priority to JP Patent Application No. 2009-256067 and JP Patent Application No. 2009-266184 based thereon, the specification and/or the drawings of which are herein incorporated by reference.

Effects of the Invention

According to the roe maturity determination device and the roe maturity determination method of the present invention, maturity of roe is determined on the basis of an image of light passing through the roe, and therefore the maturity of roe can be always determined uniformly. Accordingly the quality of the roe can be made stable.

DETAILED DESCRIPTION OF THE PREFERRED EMBODIMENTS

<Embodiment 1>

The following describes embodiments of the present invention, with reference to the drawings. Although the following embodiments exemplify pollack roe, the roe is not limited to pollack roe and may be other roe.

Figure 1:
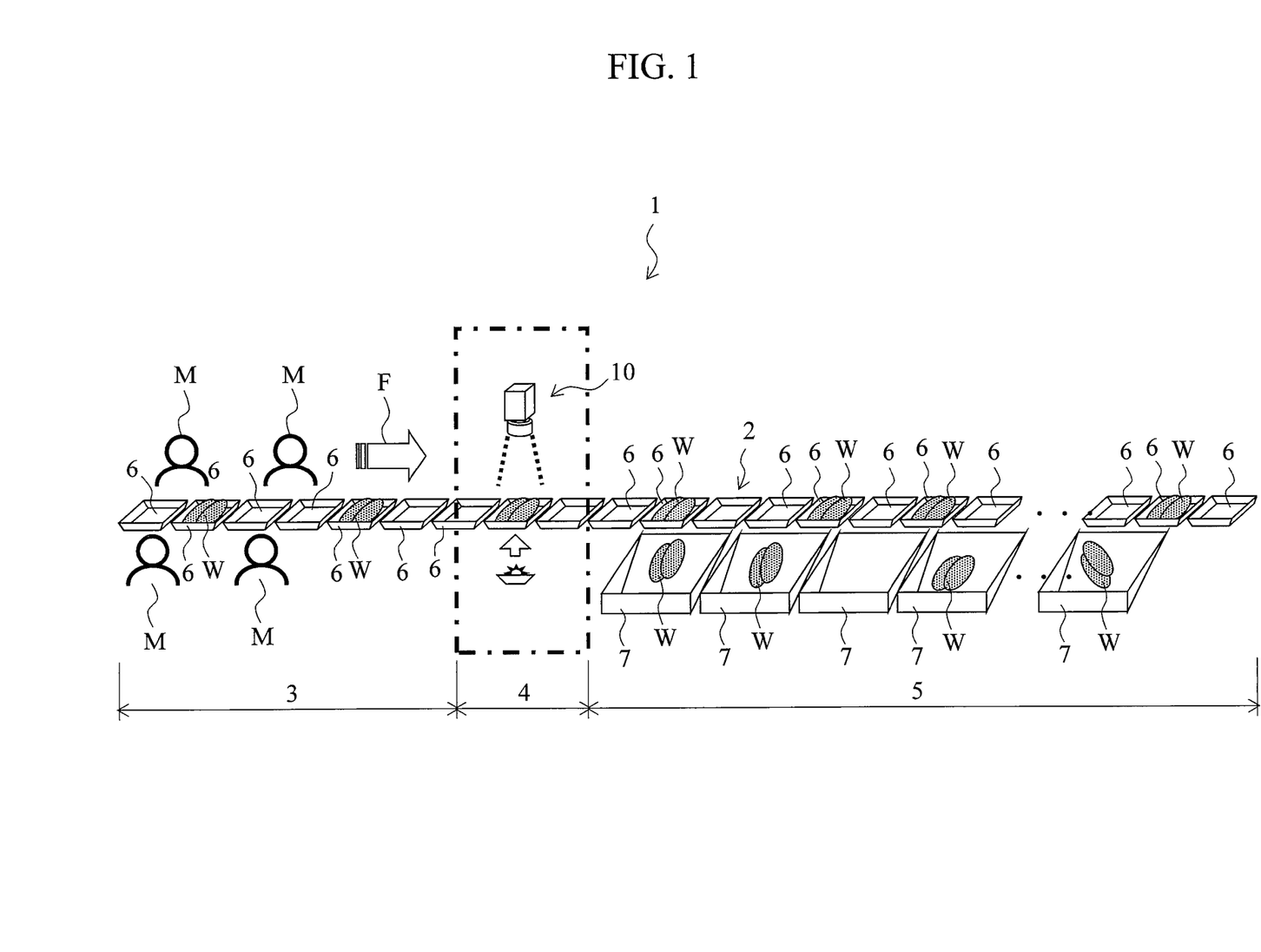
FIG. 1 explains the configuration of a roe selection device provided with a roe maturity determination device of the present invention.

FIG. 1 schematically illustrates the configuration of a roe selection device provided with a roe maturity determination device of the present invention.

As illustrated in FIG. 1, a roe selection device 1 includes a conveyance line 2 such as a conveyor, and includes an input portion 3, a classification portion 4 and an output sort portion 5 along the conveyance line 2 in this stated order from upstream.

The conveyance line 2 is provided with loading trays (loading portion) 6 disposed continuously in a conveyance direction F, away from each other at predetermined intervals. The loading tray 6 includes a plate member made of a light transmissive material such as synthetic resin, and is shaped like a flat dish capable of loading pollack roe W side by side thereon. The conveyance line 2 is configured to convey the loading trays 6 with pollack roe W loaded thereon continuously toward the downstream of the conveyance direction F.

The input portion 3 receives pollack roe W to be input to the conveyance line 2. In the present embodiment, an operator M manually loads pollack roe W on the loading trays 6.

At the classification portion 4 is performed processing to determine a class of pollack roe W. The class is determined on the basis of predetermined criteria such as shapes, colors, maturity and weight of the pollack roe W. Then, the maturity as one of factors for classification is determined using a roe maturity determination device 10 of the present invention.

At the output sort portion 5 is performed selection processing where pollack roe W is sorted on the basis of the determination result by the classification portion 4 and is output. In the present embodiment, a plurality of output trays 7 is disposed side by side for each class along the conveyance line 2. As a loading tray 6 with pollack roe W loaded thereon is conveyed to the position of an output tray 7 of the corresponding class, the loading tray 6 is slanted from the loading position state to an output position state so as to let the pollack roe W out from the loading tray 6 to the output tray 7.

Figure 2:
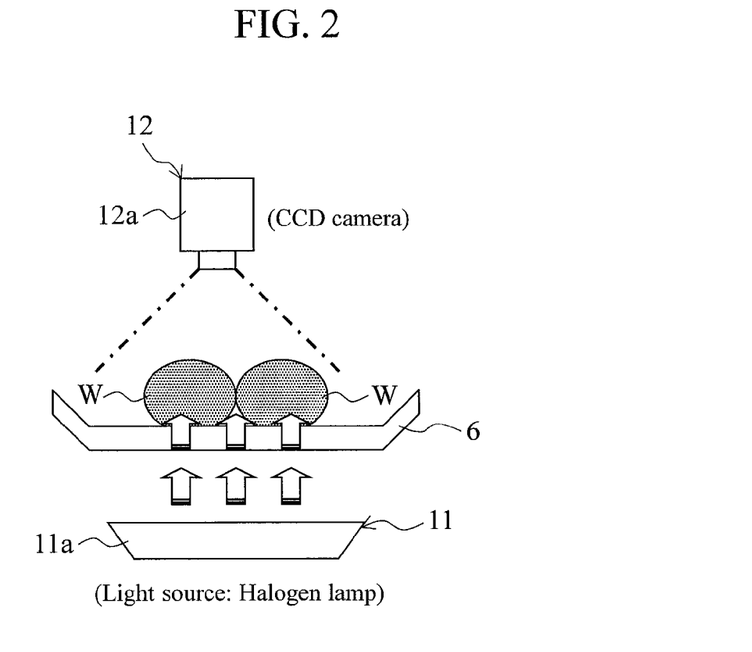
FIG. 2 explains the configuration of the roe maturity determination device in Embodiment 1.
Figure 3:
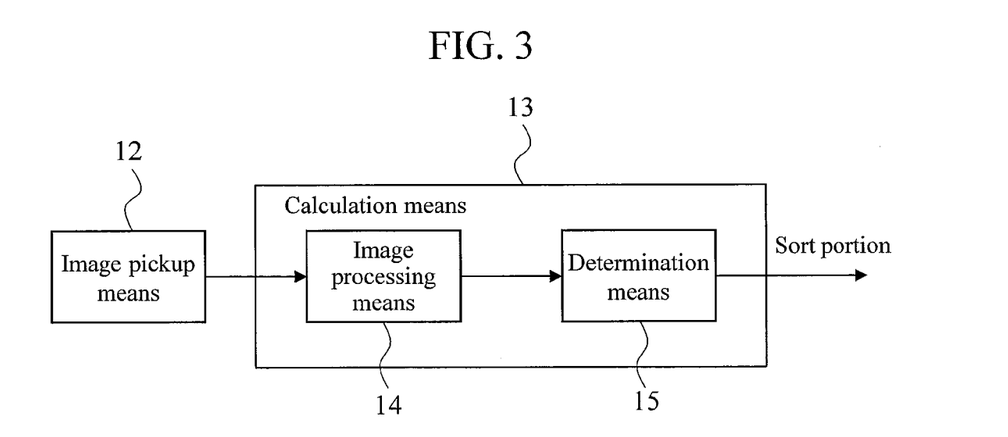
FIG. 3 is a functional block diagram of the roe maturity determination device in Embodiment 1.

FIG. 2 explains the configuration of the roe maturity determination device of the present invention, and FIG. 3 is a functional block diagram of the roe maturity determination device.

The roe maturity determination device 10 includes light irradiation means 11 to irradiate pollack roe W loaded on a loading tray 6 with light; image pickup means 12 that takes an image of light irradiated from the light irradiation means 11 and passing through the pollack roe W and calculation means 13 that performs image processing of the image taken by the image pickup means 12 and determines maturity of the pollack roe W on the basis of a result of the image processing.

The light irradiation means 11 includes a light source 11a such as a halogen lamp. As illustrated in FIG. 2, the light source 11a is disposed below a loading tray 6, and is directed so as to emit light upward. The light source 11a used has capacity of irradiating with light of an amount enough to pass through a loading tray 6 and pollack roe W. The light source 11a may be one capable of irradiating the entire pollack roe W on the loading tray 6 with uniform brightness of light, and is not limited to a halogen lamp.

The image pickup means 12 includes a CCD camera 12a capable of taking a color image. The CCD camera 12a is disposed above a loading tray 6 so as to be opposed to the light source 11a, and various settings therefor such as focusing, aperture and shutter speed are correctly made so that an image of the pollack roe W on the loading tray 6 can be taken from above the loading tray 6. Then, as pollack roe W loaded on a loading tray 6 is conveyed, an image of light irradiated from the light source 11a of the light irradiation means 11 and passing through the pollack roe W via the loading tray 6 can be taken.

The calculation means 13 includes combination of hardware such as a computer and a software program. The software program is executed on the hardware, whereby image processing means 14 and determination means 15 are implemented as an internal function of the calculation means 13 as illustrated in FIG. 3.

The image processing means 14 performs image processing of an image taken to extract an image of the pollack roe W only from the image taken, thus creating an image of the roe, and measures a light transmissive value of light passing through the pollack roe W on the basis of the created roe image. The image processing means 14 calculates an average of the light transmissive values transmitting through a predetermined area range.

Figure 4:
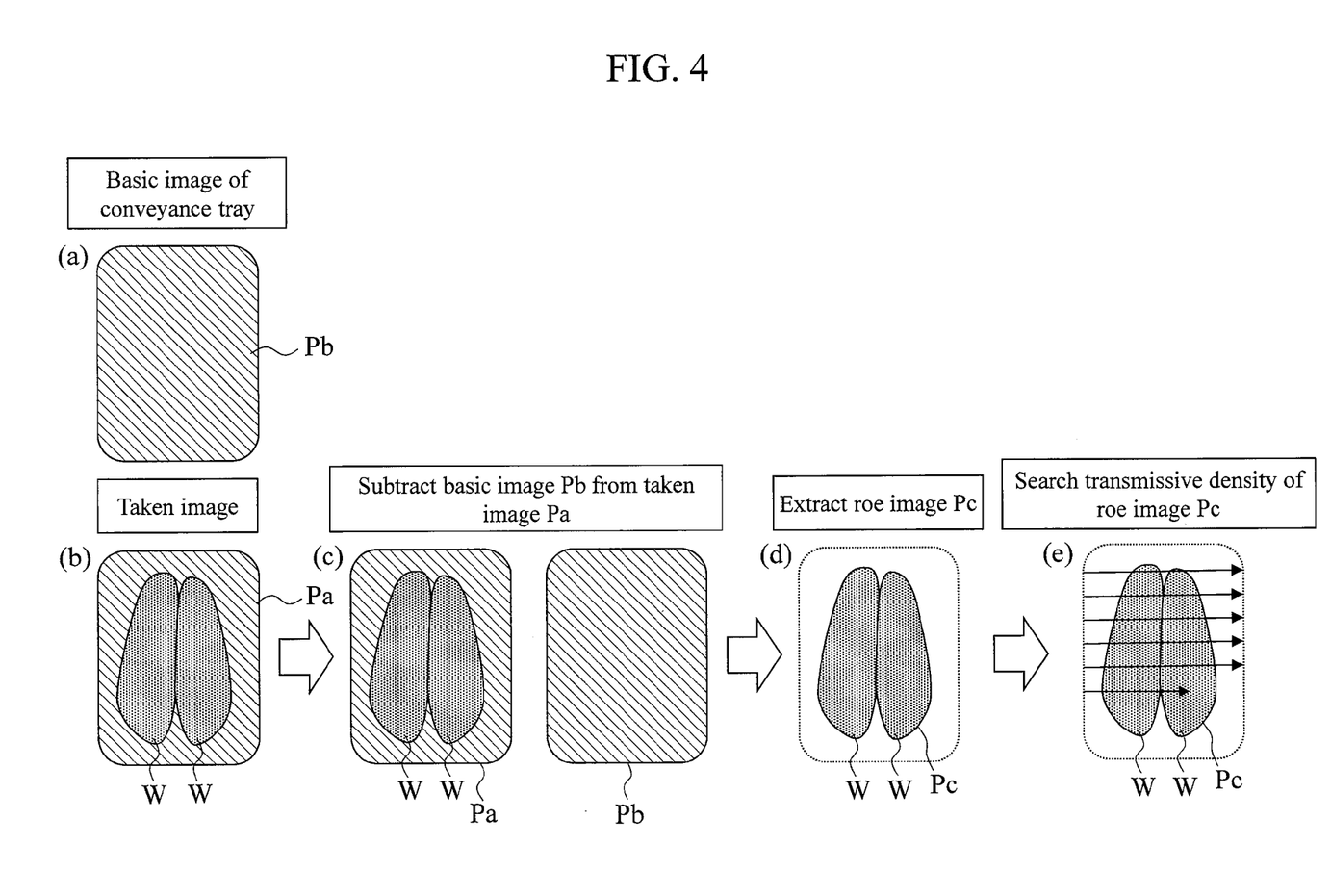
FIG. 4 explains image processing in Embodiment 1.

FIG. 4 illustrates exemplary image processing by the image processing means.

Firstly, the image pickup means 12 takes an image of an empty loading tray 6 without pollack roe W loaded thereon beforehand, and the image is stored in storage means (not illustrated) of the calculation means 13 as a basic image Pb of the loading tray 6 (see FIG. 4(a)). Herein, light is applied from the light irradiation means 11 and an image of the light from the light source 11a passing through the loading tray 6 is taken.

Next, light is irradiated from the light irradiation means 11 to the loading tray 6 with pollack roe W loaded thereon, and an image of the light irradiated from the light irradiation means 11 and passing through the pollack roe W is taken by the image pickup means 12, thus acquiring an image Pa (see FIG. 4(b)).

Then, the image processing means 14 performs image processing to subtract the basic image Pb of the loading tray 6 from the taken image Pa (see FIG. 4(c)), and creates a roe image Pc of the pollack roe W extracted from the taken image Pa (see FIG. 4(d)). Then, on the basis of the roe image Pc, light transmissive values of the light passing through the pollack roe W are measured.

Conventionally maturity of pollack roe W is determined from the appearance. Therefore, in order to match with the appearance, a light transmissive value of the light passing through a predetermined area range of pollack roe W is found. As the predetermined area range of the pollack roe W, the light transmissive values of the light passing through the entire pollack roe W may be calculated, for example. To this end, density values of lightness of the roe image Pc are searched (see FIG. 4(e)). Then, a histogram of the density values of lightness is created, and an average of the histogram is calculated as an average of the light transmissive values.

Figure 5:
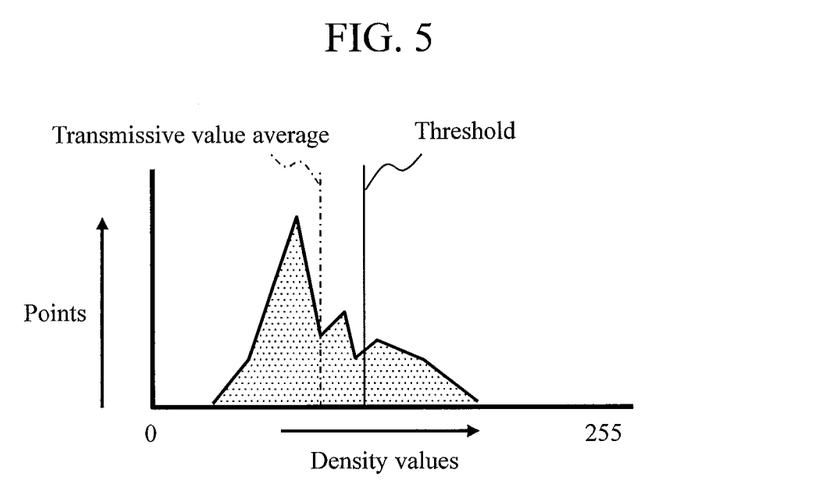
FIG. 5 is a histogram of light transmissive values of mature pollack roe.
Figure 6:
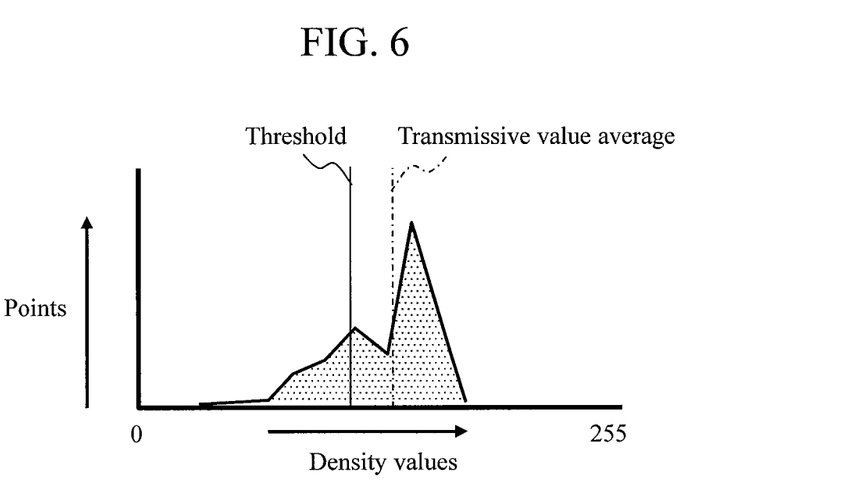
FIG. 6 is a histogram of light transmissive values of post-mature pollack roe.

FIG. 5 and FIG. 6 are histograms each representing a searching result of the density values of lightness, where FIG. 5 is a histogram of mature pollack roe and FIG. 6 is a histogram of post-mature pollack roe.

When pollack roe W is mature, the roe contains less water inside, and so the density values of lightness thereof become small. Therefore as illustrated in FIG. 5, the average of the density values is low. On the other hand, when the pollack roe W is post-mature, the inside thereof is watery, and therefore the density values of lightness become large. Therefore as illustrated in FIG. 6, the average of the density values is high.

FIG. 5 and FIG. 6 exemplify the case using brightness values of lightness (0 to 255-step gradation) as the light transmissive values. The light transmissive values, however, are not limited to brightness values of lightness, and they may be at least one of lightness, color saturation and hue.

The determination means 15 determines maturity of the pollack roe W on the basis of the light transmissive values measured by the image processing means 14. More specifically, the determination means 15 compares the average of the light transmissive values with a predetermined threshold, and determines, on the basis of a comparison result, whether the pollack roe W is mature or post-mature. Specifically, when the average is lower than the threshold, the determination means 15 determines the pollack roe W as mature, and when the average is the threshold or more, the determination means 15 determines the pollack roe W as post-mature. The threshold may be set freely.

Alternatively, the determination means 15 may decide maturity of pollack roe W by determining to which one of a plurality of predetermined maturity ranks the average of the light transmissive values corresponds. For instance, the plurality of maturity ranks used may include three types of maturity ranks of a premature roe rank, a mature roe rank and a post-mature roe rank, and the maturity of pollack roe W may be decided using the maturity ranks. Determination may be made to which one of predetermined light transmissive value regions, each corresponding to the premature roe rank, the mature roe rank or the post-mature roe rank, the average of the light transmissive values corresponds, and on the basis of the determination result, determination may be made as to whether the pollack roe W is premature, mature or post-mature.

According to the aforementioned roe maturity determination device 10, an image of light irradiated from the light irradiation means 11 and passing through pollack roe W is taken to acquire an image Pa, and on the basis of the taken image Pa, maturity of the pollack roe W is determined. Therefore, a uniform determination result can be always obtained. Accordingly, the quality of pollack roe W can be made stable.

Further the maturity is determined using the average of light transmissive values of the light passing through a predetermined range area of the pollack roe W, and therefore the determination result can be matched with the actual looking (appearance determination) and so a natural determination result can be obtained.

The roe maturity determination device 10 enables full-automatic selection operation of pollack roe W using a mechanical device and without human power. This can lead to labor savings, thus eliminating securing of manpower and reducing personnel costs.

<Embodiment 2>

Figure 7:
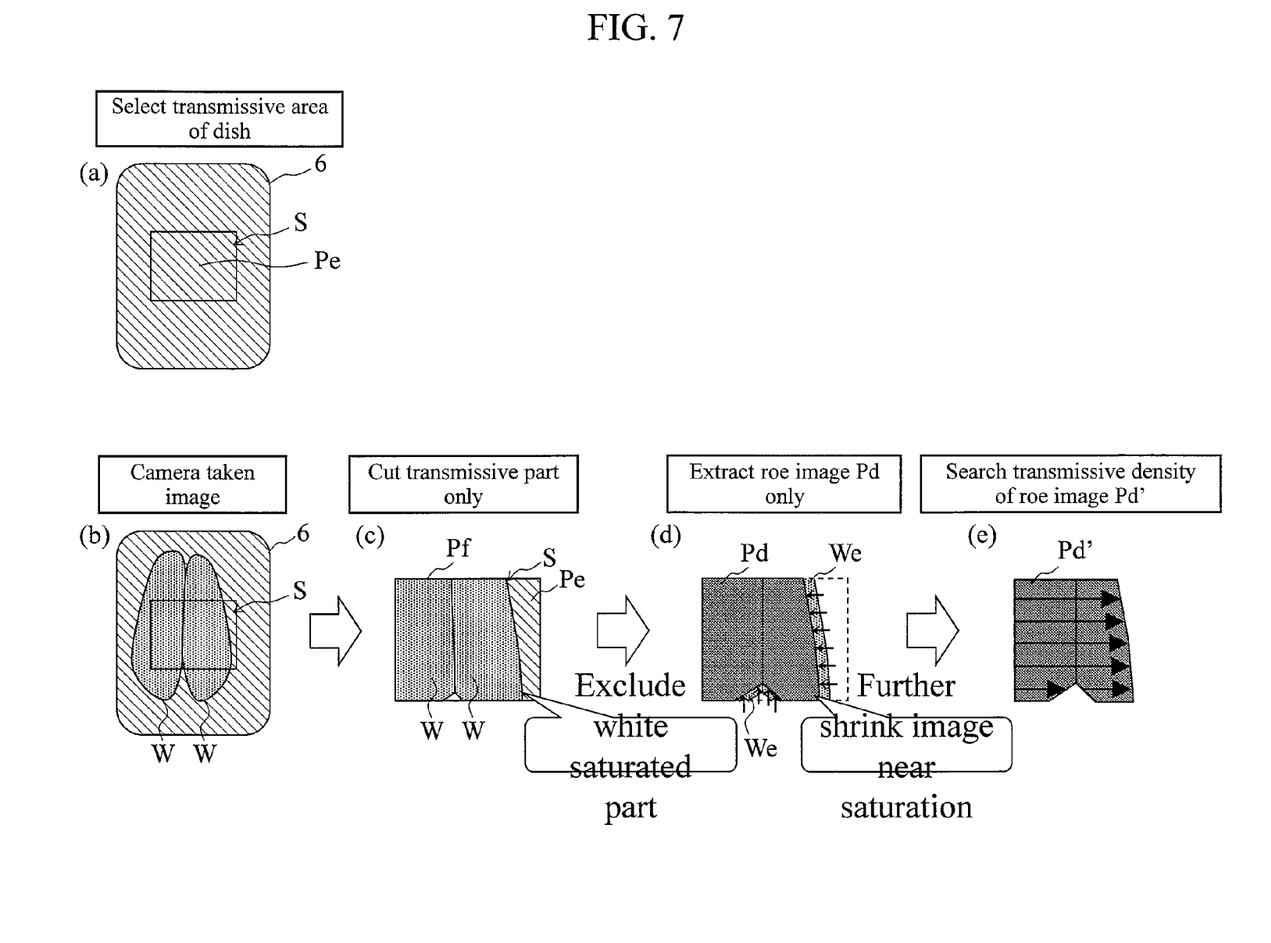
FIG. 7 explains image processing in Embodiment 2.

The following describes Embodiment 2, with reference to FIG. 7.

The aforementioned Embodiment 1 exemplifies the case where the light transmissive amount of the light passing through the entire pollack roe W is calculated to determine the light transmissive amount of the light passing through a predetermined area range of the pollack roe W. Embodiment 2, however, has a feature that a light transmissive amount is calculated for light passing through at least a part of the pollack roe W.

Firstly, an image of an empty loading tray 6 without pollack roe W loaded thereon is taken at a region S of a predetermined range by the imaging means 12, and the taken image is stored in storage means (not illustrated) of the calculation means 13 as a basic image Pe (see FIG. 7(a)).

For the image pickup, an image of the light irradiated from the light irradiation means 11 in a state of the light from the light source 11a passing through the loading tray 6 is taken. The region S may be set so that at least a part of the pollack roe W loaded on the loading tray 6 is disposed in the region S, and in the present embodiment, the region S is set at a substantially center portion of the loading tray 6.

Next, for maturity determination, light is applied from the light irradiation means 11 to the loading tray 6 with pollack roe W loaded thereon (see FIG. 7(b)), and an image of the light irradiated from the light irradiation means 11 and passing through the pollack roe W at the region S is taken by the image pickup means 12.

The image processing means 14 acquires an image Pf at the region S taken by the image pickup means 12, and performs image processing to subtract the basic image Pe of the loading tray 6 that is saturated as white from the taken image Pf (see FIG. 7(c)), thus cutting a partial image Pd of the pollack roe W only from the image Pf at the region S.

Then, image processing is performed so that an image of the partial image Pd of the pollack roe W is shrunk at a saturation adjacent part We by a few dots, thus creating a roe image Pd' (see FIG. 7(d)). Then, on the basis of the roe image Pd', a light transmissive value of light passing through the pollack roe W is measured. The measurement processing of the light transmissive value following the aforementioned image processing is similar to that of Embodiment 1, and therefore the detailed descriptions thereon are omitted.

According to the present embodiment, as compared with Embodiment 1 performing image processing of the entire pollack roe W, the image processing range can be narrowed, and therefore the information amount of the image processing can be reduced. Therefore, the processing can be speeded up, and a cycle time can be shortened. Further, since the light transmissive value is limitedly measured only at the desired region S, influences by light and dark parts formed by a rib or the like of the loading tray 6, for example, can be eliminated, and the light transmissive value of just pollack roe W can be precisely measured.

<Experimental Examples>

Figure 8:
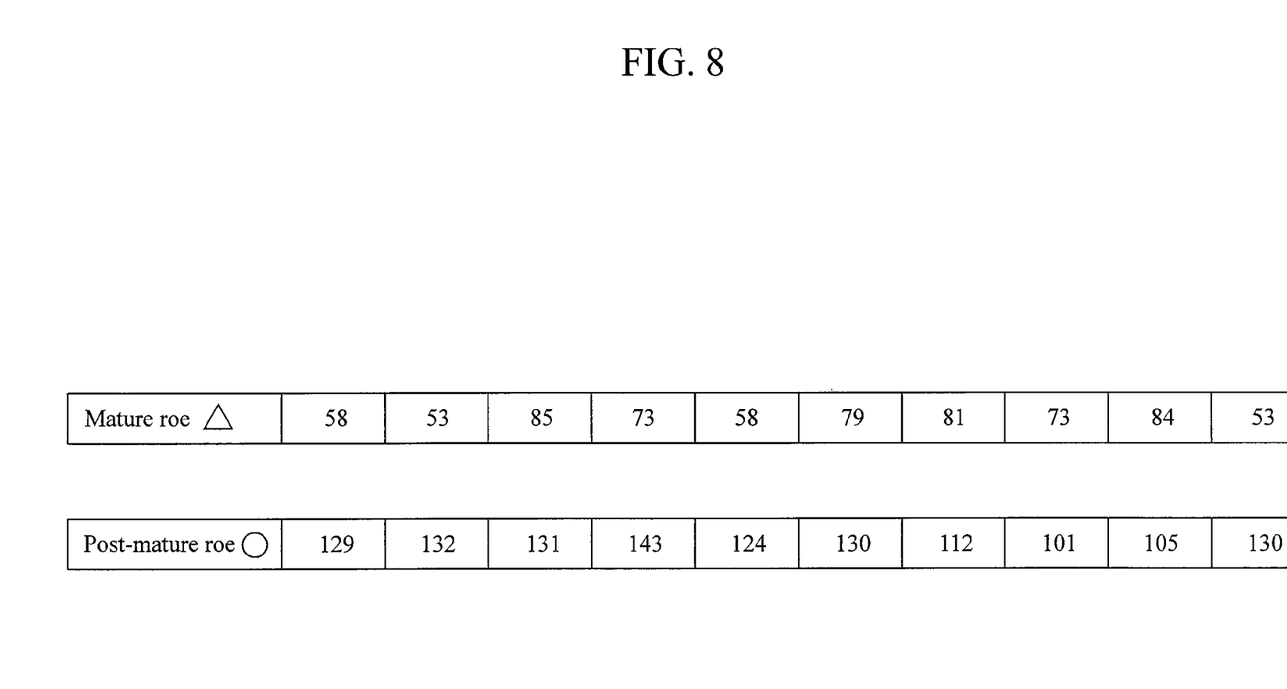
FIG. 8 is a table illustrating experimental data.
Figure 9:
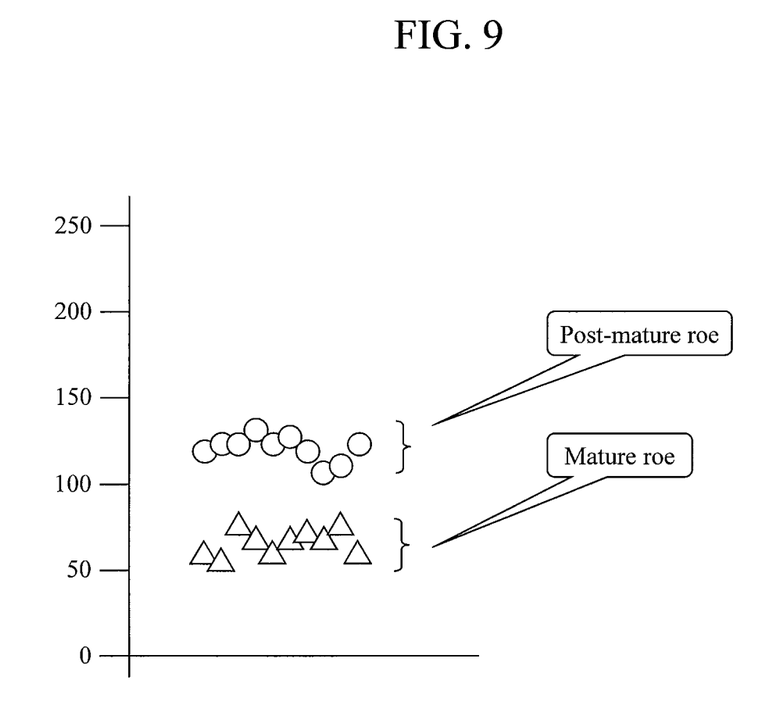
FIG. 9 is a graph illustrating experimental data.

FIG. 8 and FIG. 9 illustrate experimental data on mature and post-mature pollack roe. FIG. 8 is a comparison table of the experimental data, and FIG. 9 is a graph based on the experimental data of FIG. 8.

In this experimental example, ten pollack roe samples were prepared for each of mature and post-mature roe, and light transmissive values of these samples were measured with the roe maturity determination device of the present invention. As a result, as illustrated in FIG. 8, the mature pollack roe showed light transmissive values around 60, and the post-mature pollack roe showed values around 120. In this way, there was a difference around twice in their light transmissive values between the mature pollack roe and the post-mature pollack roe, and as illustrated in FIG. 9, a clear difference was shown between the mature pollack roe and the post-mature pollack roe. Therefore, it was found that maturity of pollack roe can be clearly determined on the basis of light transmissive values.

The present invention is not limited to the aforementioned embodiments, and can be modified variously in the range without departing from the scope of the present invention. For instance, although the aforementioned embodiments describe the case where the loading trays 6 are exemplified as the loading portion, the loading portion may be a conveyance belt of a belt conveyor.

The aforementioned embodiments exemplify the case using a color CCD capable of taking a color image as the image pickup means. Instead, a camera capable of taking a monochrome image may be used. A color CCD used enables detection of transmissive colors using three faces of RGB and enables setting of various algorithms as an option. On the other hand, a monochrome camera used can reduce costs for the image pickup means, and can reduce an information amount than color images, can facilitate image processing and determination processing and can improve processing speed.

<Embodiment 3>

Figure 10:
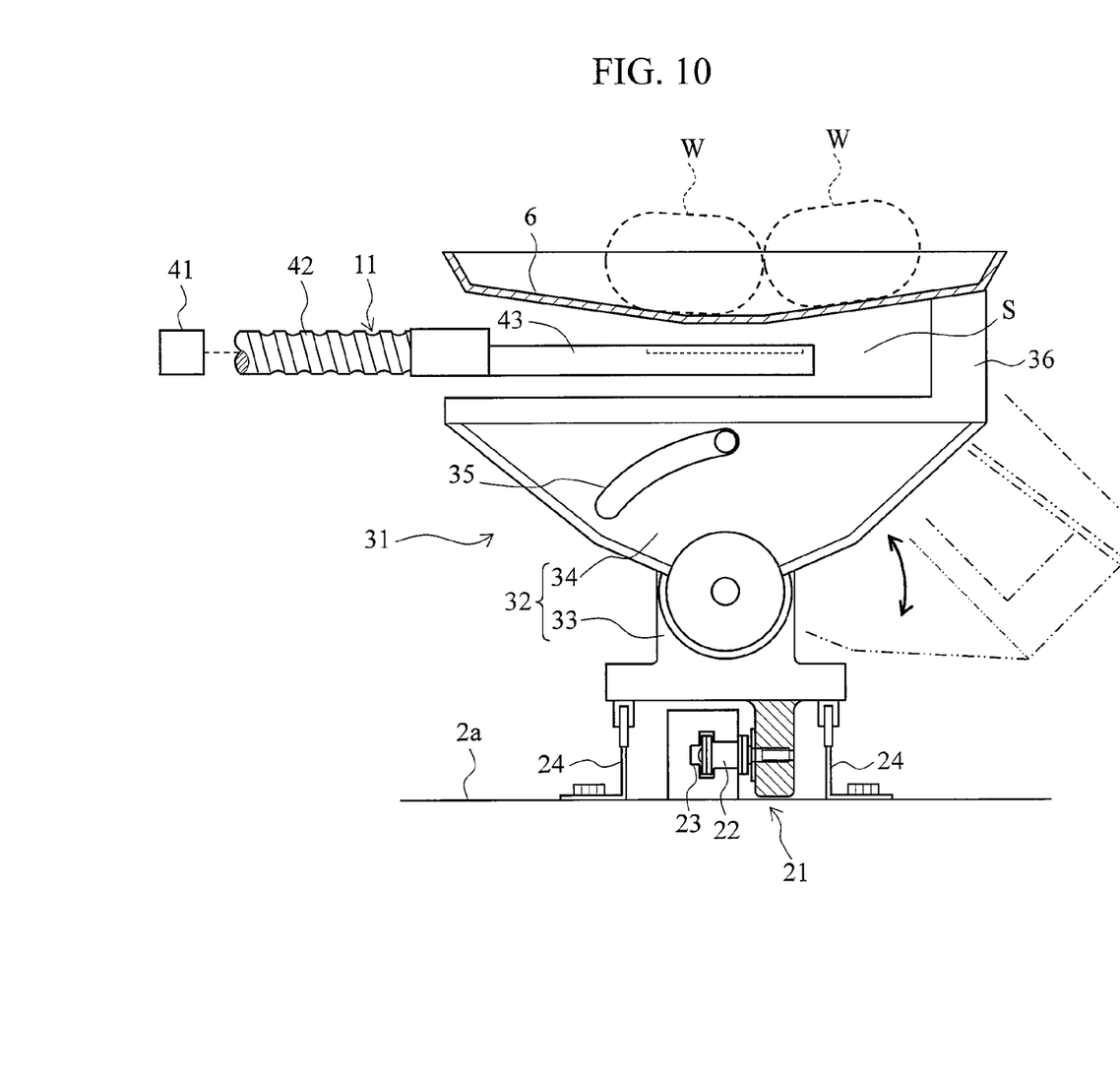
FIG. 10 explains the configuration of a roe maturity determination device in Embodiment 3.

The following describes Embodiment 3 of the present invention, with reference to FIG. 10.

FIG. 10 explains the configuration of a roe maturity determination device of Embodiment 3. Same reference numerals are assigned to elements similar to those of the aforementioned embodiments to omit their detailed descriptions.

Similarly to Embodiments 1 and 2, a roe maturity determination device 10 of Embodiment 3 is configured to irradiate pollack roe W with light from below the pollack roe W, take an image of the irradiated light passing through the pollack roe W from above the pollack roe W, and determine maturity of the pollack roe W on the basis of the taken image. The roe maturity determination device 10 includes a loading tray 6, conveyance means 21, supporting means 31 and light irradiation means 11.

The conveyance means 21 is provided along a conveyance line 2 (see FIG. 1), and is configured to move horizontally below a loading tray 6 to convey the loading tray 6. As illustrated in FIG. 10, the conveyance means 21 includes a chain conveyor 22 in the present embodiment. The chain conveyor 22 is supported guidably by a guiding member 23 between a pair of left and right rails 24 provided on a line table 2a of the conveyance line 2 and is rotary-driven by a driving motor not illustrated so as to move a conveyance direction of the loading tray 6 along a top face of the line table 2a.

The supporting means 31 is provided between the conveyance means 21 and the loading tray 6 to support the loading tray 6 above the conveyance means 21 and forms a space S between the conveyance means 21 and the loading tray 6, the space S extending over the conveyance direction of the loading tray 6 and having one opening side (in FIG. 10, the left side) in the lateral direction with reference to the conveyance direction.

The supporting means 31 includes slanting means 32 to slant the loading tray 6 in the lateral direction at the output sort portion 5, for example, the slanting means 32 being capable of changing the position of the loading tray 6 from a loading position state (the state illustrated with the solid lines in FIG. 10) to load pollack roe W on the loading tray 6 to an output position state (the state illustrated with the phantom lines in FIG. 10) to let the pollack roe W out to a side of the conveyance means 21.

The slanting means 32 includes a base 33 coupled with the chain conveyor 22 so as to slide on the rails 24, a movable portion 34 horizontally swingably supported above the base 33 around the same direction as the conveyance direction of the loading tray 6 as a rotation axis, and alignment means 35 to control the swing of the movable portion 34 with reference to the base 33 for alignment so as to enable selectively change of the position of the loading tray 6 between the loading position state and the output position state.

The supporting means 31 includes a supporting leg 36 to support the loading tray 6 above the slanting means 32. The supporting leg 36 is provided between the movable portion 34 of the slanting means 32 and the loading tray 6 and is positioned on the other side of the lateral direction with reference to the conveyance direction (In FIG. 10, the right side) to form the space S above the slanting means 32 and below the loading tray 6.

The light irradiation means 11 is disposed at a height between the conveyance means 21 and the loading tray 6 to protrude from one side of the lateral direction of the loading tray 6 to the other side of the lateral direction so that the light irradiation means 11 can pass through the space S, and the light irradiation means 11 emits light upwardly.

The light irradiation means 11 includes a light source 41 such as a halogen lamp, a light emission portion 43 that receives light from the light source 41 and emits light and an optical fiber cable 42 to transmit light from the light source 41 to the light emission portion. The light emission portion 43 is at a height between the slanting means 32 and the loading tray 6 and has a base end supported on the one side of the lateral direction with reference to the conveyance means 21. Then, the light emission portion 43 protrudes horizontally toward the other side of the lateral direction so that a top face of a front end thereof faces the lower face of the loading tray 6. The top face of the front end is formed with a light emission face, from which light is emitted upwardly.

The light source 41 is provided at a position away from the main body of the light emission portion 43 so as to prevent transmission of heat of the light source to the loading tray 6 or the pollack roe W. The light source 41 is provided at a position higher than the loading tray 6 so as to prevent a short of a power supply for the light source due to dropping of water from the loading tray 6.

Although not illustrated especially, above the light emission portion 43 is provided an image pickup means 12 (see FIG. 2) so as to take an image of the light irradiated from the light irradiation means 11 and passing through the loading tray 6 and further passing through the pollack roe W on the loading tray 6. The configuration to determine maturity of pollack roe W on the basis of the taken image is the same as in the aforementioned Embodiments 1 and 2, and so their detailed descriptions are omitted.

According to the thus configured roe maturity determination device 10 of Embodiment 3, the supporting means 31 forms the space S between the conveyance means 21 and the loading tray 6 extending over the conveyance direction of the loading tray 6 and having one opening side of the lateral direction. The light irradiation means 11 is disposed at a height between the conveyance means 21 and the loading tray 6 to protrude from one side of the lateral direction of the tray 6 to the other side of the lateral direction so that the light irradiation means 11 can pass through the space S.

With this configuration, as the loading tray 6 is conveyed by the conveyance means 21, the light irradiation means 11 can be passed through the space S. At this time, light can be applied directly to the loading tray 6 from below the loading tray 6 so that the light can pass through the loading tray 6 and further can pass through the pollack roe W on the loading tray 6. Therefore, an image of the light irradiated from the light irradiation means 11 and passing through the pollack roe W can be taken, and maturity of the pollack roe W can be determined on the basis of the taken image.

In the case of a device configured to convey pollack roe W loaded on a belt conveyor, for example, the belt may be made of a light transmissive material, and light irradiation means may be provided below the belt so as to apply light upwardly. With this configuration, light can be passed through the belt and further can passed through pollack roe W on the belt.

On the other hand, in the case of a device as in the present invention configured to convey pollack roe W loaded on a loading tray, the loading tray has to be supported on the conveyance means. Therefore, in order to apply light from below the pollack roe W, light irradiation means has to be disposed below the conveyance means, which means a long distance from the light irradiation means and the pollack roe W, causing a problem that the light emitted from the light irradiation means decays before the arrival to the pollack roe W and light intensity thereof becomes weak. As a result, a higher-intensity light irradiation means has to be used, leading to a steep rise in equipment costs, and therefore a device at a lower cost cannot be realized.

Especially when the slanting means is provided between the conveyance means and the loading tray, the slanting means inhibits light passage, thus making it difficult to let the light emitted from the light irradiation means reach the pollack roe W.

To cope with this, according to the roe maturity determination device 10 of the present invention, the supporting leg 36 of the supporting means 31 forms the space S between the conveyance means 21 and the loading tray 6 extending over the conveyance direction of the loading tray 6 and having one opening side of the lateral direction. As the loading tray 6 is conveyed, the light irradiation means 11 can be passed through the space S. With this configuration, light can be directly applied to the loading tray 6 from below the loading tray 6.

Accordingly, the distance between the light irradiation means 11 and the pollack roe W on the loading tray 6 can be shortened, and the pollack roe W on the loading tray 6 can be irradiated with sufficient amount of light so that the light passes through the pollack roe W. Therefore, an image of the light irradiated from the light irradiation means 11 and passing through the pollack roe W can be taken easily, and maturity of the pollack roe W can be determined on the basis of the taken image. Therefore there is no need to increase light intensity of the light irradiated from the light irradiation means 11, and the size and power consumption of a light source can be suppressed for cost reduction.

Further, according to the roe maturity determination device 10 of Embodiment 3, the light irradiation means 11 includes the light source 41 such as a halogen lamp and the light emission portion 43 that receives light from the light source 41 via the optical fiber cable 42 for light emission. Since the light source 41 is provided at a position away from the light emission portion 43, transmission of heat of the light source 41 to the loading tray 6 or the pollack roe W on the loading tray 6 can be prevented. Further since the light source 41 is provided at a position higher than the loading tray 6, even when water of pollack roe W drops and adheres to the light emission portion 43, a short of a power supply for the light source can be prevented.

The present invention is not limited to the aforementioned Embodiment 3, and can be modified variously in the range without departing from the scope of the present invention. For instance, although the aforementioned Embodiment 3 describes a chain conveyor as the conveyance means 21, the conveyance means may be other than the chain conveyor as long as it moves below the loading tray 6 to convey the loading tray 6.

All publications, Patent and Patent Applications cited in the present specification are herein incorporated by reference in their entirety.

DESCRIPTION OF REFERENCE NUMBERS

1: Roe selection device
2: Conveyance line
3: Input portion
4: Classification portion
5: Output sort portion
6: Loading tray (loading portion)
7: Output tray
10: Roe maturity determination device
11: Light irradiation means
11a: Light source
12: Image pickup means
12a: CCD camera
13: Calculation means
14: Image processing means
15: Determination means
Pa: Taken image
Pb: Basic image
Pc: Roe image
W: Pollack roe (roe)

The invention claimed is:

1. A roe maturity determination device comprising components configured to irradiate roe with light from below the roe, take an image of the irradiated light passing through the roe from above the roe and determine maturity of the roe on a basis of the image, the device further comprising:
a loading tray comprising a light transmissive material, on which the roe is loaded;
a conveyor that moves horizontally below the loading tray to convey the loading tray in a conveyance direction;
a support comprising a rotatable portion configured to slant the loading tray in a lateral direction orthogonal to the conveyance direction, the rotatable portion capable of changing a position of the loading tray from a loading position to load the roe thereon to an output position to let the roe out to a side of the conveyor, the support between the conveyor and the loading tray and supporting the loading tray above the conveyor, the support further defining a space between the conveyor and the loading tray, the space extending over the conveyance direction of the loading tray and having one open side in the lateral direction; and
a light irradiation device disposed at a height between the conveyor and the loading tray and extending in the lateral direction into the space through the open side, the light irradiation device including a light emission portion extending from one side of the loading tray to the other side of loading tray in the lateral direction, such that irradiated light from the light emission portion passes through the space.

2. The roe maturity determination device according to claim 1 further comprising:
a camera that takes an image of light irradiated from the light irradiation device and passing through the roe; and
a programmed computer configured to determine maturity of the roe on a basis of the image taken by the camera.

3. The roe maturity determination device according to claim 2, wherein the programmed computer executes software to
process the image to extract an image including at least a part of the roe from the taken image, thus creating a roe image, and to measure, on a basis of the created roe image, a light transmissive value of light passing through the roe, and to determine the maturity on a basis of the light transmissive value measured by the image processing means.

4. The roe maturity determination device according to claim 3, wherein the light transmissive value comprises at least one of lightness, color saturation and hue.

5. The roe maturity determination device according to claim 3, wherein programmed computer calculates an average of light transmissive values of light passing through a predetermined area range of the roe on a basis of the roe image, and determines the maturity of the roe on a basis of the average of light transmissive values calculated by the image processing means.

6. The roe maturity determination device according to claim 5, wherein the programmed computer compares the average with a predetermined threshold to determine, on a basis of a result of the comparison, whether the roe is mature or post-mature.

7. The roe maturity determination device according to claim 6, wherein when the average is lower than the threshold, the programmed computer determines that the roe is mature, and when the average is the threshold or higher, determines that the roe is post-mature.

8. The roe maturity determination device according to claim 5, wherein the programmed computer determines to which one of a plurality of predetermined maturity ranks the average corresponds, and decides, on a basis of a result of the determination, the maturity of the roe.

9. The roe maturity determination device according to claim 8, wherein the programmed computer executes software that includes three types of maturity ranks including a premature roe rank, a mature roe rank and a post-mature roe rank as the plurality of maturity ranks to determine the maturity of the roe.

10. The roe maturity determination device according to claim 9, wherein the programmed computer determines to which one of light transmissive value regions, each corresponding to the premature roe rank, the mature roe rank or the post-mature roe rank, the average corresponds, and determines, on a basis of a result of the determination, that the roe is any one of the premature roe, the mature roe and the post-mature roe.

11. The roe maturity determination device according to claim 1, wherein the loading tray includes a plate member made of a light transmissive material, the light irradiation device irradiates the loading tray with light from below the loading tray, and the camera takes the image from above of the loading tray.

12. The roe maturity determination device according to any one of claim 2, wherein camera takes a color image as the image.

13. The roe maturity determination device according to claim 1, wherein light irradiation device further includes: a light source; and an optical fiber cable that transmits the light from the light source to the light emission portion.

14. The roe maturity determination device according to claim 13, wherein the light source of the light irradiation device is disposed at a position higher than the loading tray.

15. The roe maturity determination device according to claim 13 further comprising a line table having a pair of rails, and wherein the support further comprises a base supporting the rotatable portion and having a guide member that engages the conveyer and the pair of line rails.

16. The roe maturity determination device according to claim 15, wherein the support further comprises a leg that extends from the base and supports the loading tray over the space.

* * * * *